US008926668B2

(12) United States Patent
Douget

(10) Patent No.: US 8,926,668 B2
(45) Date of Patent: Jan. 6, 2015

(54) ANCHOR FOR ATTACHMENT TO A BONY STRUCTURE

(71) Applicant: Zimmer Spine, La Cite Mondiale (FR)

(72) Inventor: Stephane Douget, Le Bouscat (FR)

(73) Assignee: Zimmer Spine, Bordeaux (FR)

( * ) Notice: Subject to any disclaimer, the term of this patent is extended or adjusted under 35 U.S.C. 154(b) by 0 days.

(21) Appl. No.: 13/772,476

(22) Filed: Feb. 21, 2013

(65) Prior Publication Data

US 2013/0150892 A1 Jun. 13, 2013

Related U.S. Application Data

(63) Continuation of application No. PCT/EP2011/064620, filed on Aug. 25, 2011.

(30) Foreign Application Priority Data

Aug. 25, 2010 (EP) ..................................... 10305916

(51) Int. Cl.
A61B 17/70 (2006.01)
A61B 17/84 (2006.01)
A61B 17/56 (2006.01)

(52) U.S. Cl.
CPC ........... *A61B 17/842* (2013.01); *A61B 17/7043* (2013.01); *A61B 17/56* (2013.01)
USPC ............................ 606/263; 606/246; 606/276

(58) Field of Classification Search
USPC ............. 606/60, 61, 246, 263, 276, 330, 279, 606/300–321
See application file for complete search history.

(56) References Cited

U.S. PATENT DOCUMENTS 2,049,361 A 7/1936 Johan
4,570,618 A 2/1986 Wu
5,030,220 A 7/1991 Howland
(Continued)

FOREIGN PATENT DOCUMENTS

EP 1205152 B1 9/2004
EP 2047813 A1 4/2009
(Continued)

OTHER PUBLICATIONS

U.S. Appl. No. 13/384,180, filed Jan. 13, 2012 (31 pgs.).
(Continued)

Primary Examiner — Mary Hoffman
Assistant Examiner — Christina Negrellirodrigue
(74) Attorney, Agent, or Firm — Seager, Tufte & Wickhem, LLC

(57) ABSTRACT

A spine stabilization system including a first anchor, a second anchor and a rod for connecting the first and second anchors together. The first anchor includes an anchor body and a hook. A slot is defined between the hook and a first wall of the anchor body, facing the hook, the slot being configured to receive a bony structure. The first anchor further comprises a flexible member having first and second ends, and an intermediate portion therebetween. The anchor body is provided with an exit passage from which the first and second ends extend, and a loop passage going through the first wall and facing the hook, the intermediate portion extending from the loop passage to form a loop going through the slot and around the bony structure.

18 Claims, 5 Drawing Sheets

(56) References Cited

U.S. PATENT DOCUMENTS

| | | | |
|---|---|---|---|
| 5,304,178 A | 4/1994 | Stahurski | |
| 5,454,812 A | 10/1995 | Lin | |
| 5,772,663 A | 6/1998 | Whiteside et al. | |
| RE36,221 E | 6/1999 | Breard | |
| 5,935,133 A | 8/1999 | Wagner et al. | |
| 5,964,769 A | 10/1999 | Wagner et al. | |
| 6,053,921 A | 4/2000 | Wagner et al. | |
| 6,086,590 A | 7/2000 | Margulies et al. | |
| 6,179,838 B1 | 1/2001 | Fiz | |
| 6,277,120 B1 | 8/2001 | Lawson | |
| 6,299,613 B1 | 10/2001 | Ogilvie et al. | |
| 6,309,390 B1 | 10/2001 | Le Couedic et al. | |
| 6,391,030 B1 | 5/2002 | Wagner et al. | |
| 6,514,255 B1 | 2/2003 | Ferree | |
| 6,547,790 B2 | 4/2003 | Harkey, III et al. | |
| 6,605,091 B1 | 8/2003 | Iwanski | |
| 6,682,533 B1 | 1/2004 | Dinsdale et al. | |
| 6,695,852 B2 | 2/2004 | Gleason | |
| 7,481,828 B2 | 1/2009 | Mazda et al. | |
| 7,959,654 B2 | 6/2011 | Mazda et al. | |
| 8,128,635 B2 | 3/2012 | Belliard et al. | |
| 2002/0116013 A1 | 8/2002 | Gleason et al. | |
| 2004/0111091 A1* | 6/2004 | Ogilvie et al. | 606/73 |
| 2008/0058818 A1 | 3/2008 | Schwab | |
| 2009/0105715 A1 | 4/2009 | Belliard et al. | |
| 2009/0138048 A1 | 5/2009 | Baccelli et al. | |
| 2009/0177233 A1 | 7/2009 | Malek | |
| 2009/0182379 A1 | 7/2009 | Baccelli et al. | |
| 2009/0248077 A1 | 10/2009 | Johns | |
| 2009/0326585 A1* | 12/2009 | Baccelli et al. | 606/263 |
| 2010/0137913 A1 | 6/2010 | Khatchadourian et al. | |
| 2010/0249845 A1 | 9/2010 | Meunier et al. | |
| 2011/0034956 A1 | 2/2011 | Mazda et al. | |
| 2011/0112581 A1 | 5/2011 | Clement | |
| 2011/0238118 A1 | 9/2011 | Baccelli et al. | |
| 2011/0238125 A1 | 9/2011 | Baccelli et al. | |
| 2011/0301644 A1 | 12/2011 | Belliard | |
| 2012/0022591 A1 | 1/2012 | Baccelli et al. | |
| 2012/0022592 A1 | 1/2012 | Belliard | |
| 2012/0059377 A1 | 3/2012 | Belliard | |

FOREIGN PATENT DOCUMENTS

| | | |
|---|---|---|
| EP | 2052689 B1 | 12/2011 |
| FR | 2890850 A1 | 2/2006 |
| WO | 0154599 A1 | 8/2001 |
| WO | 0209604 A1 | 2/2002 |
| WO | 0217803 A2 | 4/2002 |
| WO | 2009144663 A1 | 12/2009 |
| WO | 2011012690 A1 | 2/2011 |

OTHER PUBLICATIONS

U.S. Appl. No. 13/205,110, filed Aug. 8, 2011 (45 pgs.).

* cited by examiner

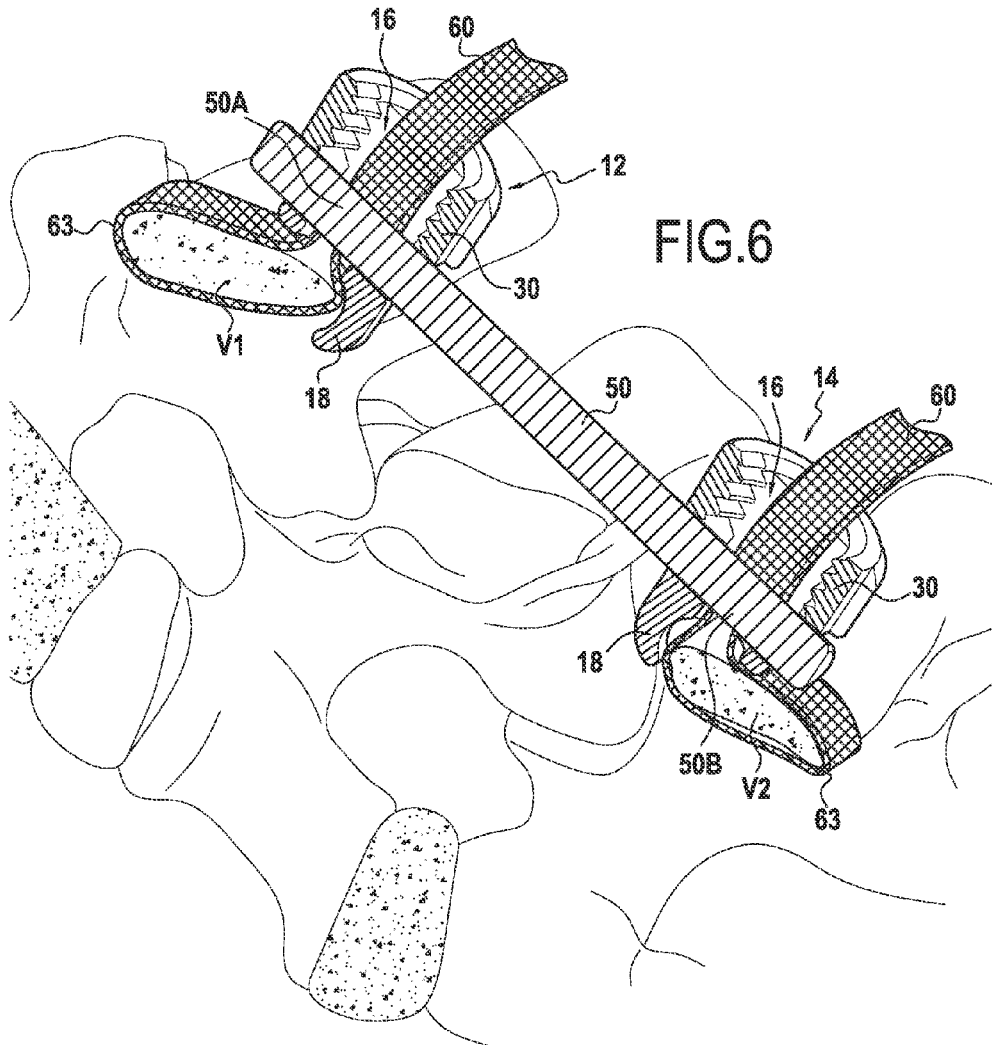
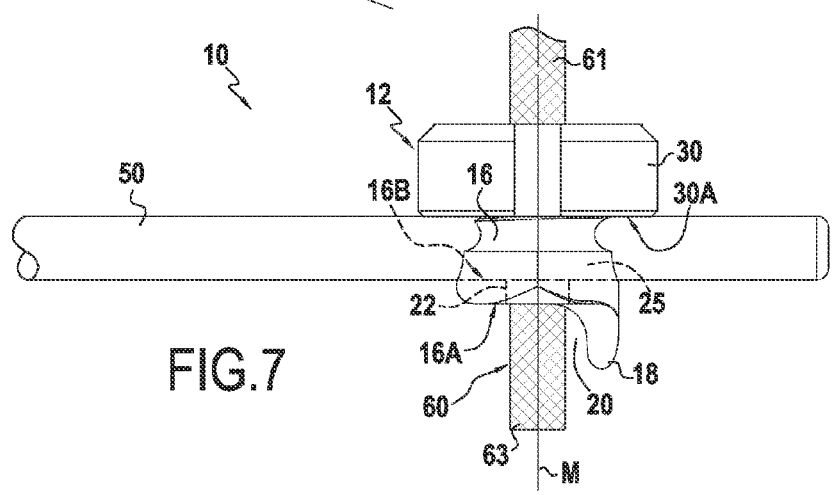

ANCHOR FOR ATTACHMENT TO A BONY STRUCTURE

CROSS-REFERENCE TO RELATED APPLICATIONS

This application is a continuation of PCT/EP2011/064620, filed on Aug. 25, 2011, which claims priority to EP10305916.8, filed on Aug. 25, 2010, the entire disclosures of which are incorporated herein by reference.

TECHNICAL FIELD

The present disclosure relates to an anchor for attachment to a bony structure, a stabilization system using such an anchor, and a method for stabilizing at least two bony structures using such a stabilization system. For instance, these system and method may be helpful for stabilizing at least two vertebrae, i.e. for holding together two vertebrae in a particular relative position, while allowing in some cases a limited amount of relative movement between the two vertebrae.

BACKGROUND

One field of application for the invention is, for instance, the treatment of scoliosis. However, the invention may also be useful to treat abnormal curvatures, deficiencies or other abnormalities of the spine, including instability of spinal segments or degenerated intervertebral discs.

The spine is formed of superposed vertebrae, normally aligned along a vertebral axis, from the sacrum (situated beneath the lumbar vertebrae) to the cervical vertebrae. Each vertebra has an anterior part, which is the vertebral body, and a posterior part, which is the vertebral arch (or neural arch), these parts enclosing the vertebral foramen.

The vertebral arch is formed by a pair of pedicles, a pair of laminae, and support articular, transverse and spinous processes. These processes project opposite to the vertebral foramen. A spinous process is also called a neural spine.

When the vertebrae are articulated with each other, the vertebral bodies form a strong pillar for the support of the head and trunk, and the vertebral foramen constitutes a canal for protecting the spinal cord (or medulla spinalis). In between every pair of vertebrae, there are two apertures called intervertebral foramina, one on either side of the vertebral axis, for passing the spinal nerves and vessels.

When the spine of a person has abnormal curvature or other deficiencies, the vertebrae are typically too close together or spaced too far apart, and there is a need to stabilize the vertebrae in the correct position relative to one another. Mainly, there is either a need to compress the vertebrae (i.e. to bring them and hold them closer together) or a need to distract the vertebrae (i.e. to space them and keep them further apart). To do this, various kinds of devices known in the art may be used.

Typically, such known devices include at least two anchors configured to be fastened, respectively, to two vertebrae, and a rod for connecting the anchors together, thereby providing stabilization between the vertebrae.

In a first kind of device, known in the art, said anchors are hooks that rest on the vertebral laminas and go along the internal wall of the vertebral foramen. Examples of such devices are disclosed, for instance, in PCT application no 2005/023126 or U.S. Pat. No. 4,269,178.

A hook has the advantage of providing a rigid and strong anchoring to the vertebra, but the physician (or other operative) may have difficulty in placing the hook correctly on the vertebra. Moreover, there is a risk that the hook may disengage from the vertebra. Such a risk sometimes leads the physician to use more hooks than necessary.

In another known example of device, disclosed in PCT application no 2009/144663, at least one of said anchors is an anchoring assembly including a body, a hook and a flexible ligament. The hook extends from the bottom face of the body. A hole is provided through the body, and extends from one lateral face of the body to the opposite lateral face. In use, the physician positions the hook on a first bony portion of a vertebra, and engages the flexible ligament through the hole so as to form a loop around a second bony portion, which is different from the first bony portion, of the same vertebra or another vertebra. A first drawback is that, the physician needs to find a convenient place for the hook and another convenient place for the flexible ligament. Moreover, since the physician applies tension to the flexible ligament after positioning the hook on the first bony portion, the flexible ligament tends to pull the body and the hook towards the second bony portion. In situations where the main direction of the tension is not aligned with the hook, this may lead to an undesired movement of the hook with respect to the first bony portion and, sooner or later, the assembly may become loosened.

In another kind of device, known in the art, said anchors are such as those disclosed in PCT application no 2009/047352. That kind of anchor comprises a blocking body and an elongate flexible member. In use, the flexible member is passed around a vertebra and through the blocking body and a rod is loaded into the blocking body. The ends of the flexible member are pulled so as to apply tension to the flexible member, and the flexible member and the rod are simultaneously fastened to the blocking body by means of the same fastening system, portion(s) of the flexible member being clamped between the rod and the blocking body. In such a system, the flexible member needs to be continuously kept under tension until the rod is fastened to the blocking body. Moreover, the flexible member may be anchored less rigidly and strongly than a hook.

SUMMARY

According to one aspect of the present disclosure, there is provided an anchor for attachment to a bony structure, the anchor comprising an anchor body, a hook and a fastening system for fastening a connection member to the anchor body; wherein a slot is defined between the hook and a first wall of the anchor body, said first wall facing the hook, this slot being configured to receive a bony structure and the hook being configured to rest on the bony structure; wherein the anchor further comprises a flexible member having a first end, a second end and an intermediate portion therebetween, the flexible member passing through the anchor body with the first and/or second end and the intermediate portion extending outside the anchor body; and wherein the anchor body is provided with at least one exit passage from which the first and/or second end extends, and at least one loop passage going through the first wall, facing the hook and, thereby, communicating with the slot, the intermediate portion extending from the loop passage to form a loop going through the slot and around said bony structure.

In an embodiment, such an anchor is a vertebral anchor, said bony structure being a vertebra.

According to another aspect of the present disclosure, there is provided a stabilization system for stabilizing at least two bony structures and, especially, two vertebrae, the system comprising: a first anchor configured to be fastened to a first vertebra, a second anchor configured to be fastened to a second vertebra, and a connection member for connecting the first and second anchors together, thereby providing stabilization between the first and second vertebrae; wherein at least the first anchor is an anchor according to the present disclosure.

Compared to the anchors and stabilization systems of the prior art, such an anchor and stabilization system are safer to use and easier to handle.

The hook provides a rigid and strong connection to the first vertebra. Moreover, it prevents any fatigue phenomena in the connection over time.

Since the loop passage goes through the first wall (which faces the hook) and communicates with the slot, the main direction of the tension of the flexible member is aligned with the hook. Thus, the flexible member improves the stability of the hook on the first vertebra. Moreover, there is no risk that the hook may disengage from the first vertebra since it is held back by the flexible member. In brief, while the flexible member provides a reliable and well-defined "static" fixation of the anchor to the vertebra, the hook comes into play to support the flexible member upon transient loads and to restrict movement allowed by the possible elastic properties of the flexible member. The connection to the first vertebra is, therefore, more reliable.

Furthermore, in use, by pulling on the end(s) of the flexible member, the physician (or other operative) brings the hook closer to the first portion of the first vertebra, which makes the positioning of the hook easier.

The flexible member may be made of any suitable material that is flexible such as a band, wire, ligament, or cord. For instance, it is made of a metal, of polymeric material or a combination thereof.

It is to be noted that the stabilization system of the disclosure may be used for providing "static stabilization" or "dynamic stabilization" between the vertebrae. Static stabilization consists in holding together two vertebrae in a particular relative position, while not allowing any movement between the two vertebrae, whereas dynamic stabilization consists in holding together two vertebrae in a particular relative position, while allowing a limited amount of relative movement between the two vertebrae. For dynamic stabilization, the flexible member and/or the connection member may have elastic properties.

In an embodiment, the intermediate portion goes along an internal face of the hook, so that the intermediate portion is fitted between the hook and the bony structure. In this embodiment, the hook does not rest directly, but indirectly, on the bony structure. This avoids direct contact between the hook and the bony structure.

In an embodiment, the hook is integral with the anchor body. This reduces the number of pieces in the stabilization system and provides a strong connection between the hook and the anchor body.

The connection member may be rigid or not. The connection member may be a rod. Otherwise, the connection member may comprise an elongate spacer with a longitudinal lumen, and an elongate member (e.g. a ligament or cord) passing through the longitudinal lumen, the elongate member being connected to the first and second vertebrae by the first and second anchors, and the spacer being enclosed by said anchors.

In an embodiment, the anchor body is provided with a main passage configured to receive a portion of the connection member.

In this embodiment, the exit passage and the loop passage communicate with the main passage, so that the flexible member passes between the first portion of the connection member and the anchor body.

One skilled in the art will appreciate that a variety of fastening systems for fastening the first portion of the connection member to the anchor body may be used, including for instance clamping or mating systems with frictional or mechanical engagement.

In an embodiment, the fastening system comprises a locking member for engagement with the anchor body, the locking member engaging with the anchor body so as to clamp the portion of the connection member inside the main passage and to clamp, at the same time, the flexible member between the anchor body and the portion of the connection member.

In an embodiment, the locking member is located opposite to the hook with respect to the connection member, which makes the locking member easier to access and, thus, makes it easier to lock the connection member and flexible member inside the anchor body.

According to another aspect of the present disclosure, there is provided a method for stabilizing at least two vertebrae, comprising the steps of:

providing a stabilization system according to the present disclosure;

impeding relative movement between the first anchor and a first vertebra by fastening the first anchor to the first vertebra, by means of said flexible member and said hook, impeding relative movement between the second anchor and a second vertebra by fastening the second anchor to the second vertebra, and impeding relative movement between the first and second anchors by connecting the first and second anchors together, by means of the connection member.

Such a method is easy to implement and has advantages derived from the use of a stabilization system according to the present disclosure.

In an embodiment, the step of fastening the first anchor to a first vertebra comprises the sub-steps of passing the flexible member around a bony portion of the first vertebra and through the anchor body, applying tension to the flexible member by pulling on its first and/or second ends and hooking the hook on said bony portion.

In this embodiment, a portion of the flexible member may be fitted between the hook and the bony portion.

In this embodiment, the connection member may be first connected to the first anchor, the connection member and the first anchor then both being brought closer to the first vertebra by applying tension to the flexible member.

Pulling on the flexible member helps the physician (or other operative) to bring the hook and the connection member closer to the first bony portion of the first vertebra. Thus, the flexible member is useful as a guide for positioning the hook and the connection member.

In an embodiment, the stabilization system is used for distracting the first and second vertebrae, the first anchor being placed so that the slot is opposite to the second anchor, with respect to the hook, i.e. the hook of the first anchor is between the second anchor and the slot of the first anchor.

In an embodiment, the stabilization system is used for compressing the first and second vertebrae, the first anchor being placed so that its slot is oriented toward the second anchor.

Other features and advantages of the present invention become apparent from the following detailed description, taken in conjunction with the attached drawings.

Except in cases of incompatibility, structures and features described with respect to one embodiment or example can similarly be applied to other embodiments or examples.

BRIEF DESCRIPTION OF THE DRAWINGS

In the drawings, like reference signs generally refer to the same parts throughout the different views. Moreover, parts of different embodiments that have analogous function are identified by the same reference numerals plus 100, 200, etc.

FIG. 6 is a sectional view showing the stabilization system of FIG. 1 in place on two vertebrae, in a distracting configuration.

FIG. 7 is a side view, analogous to FIG. 2, showing another example of stabilization system.

DETAILED DESCRIPTION

Figure 1:
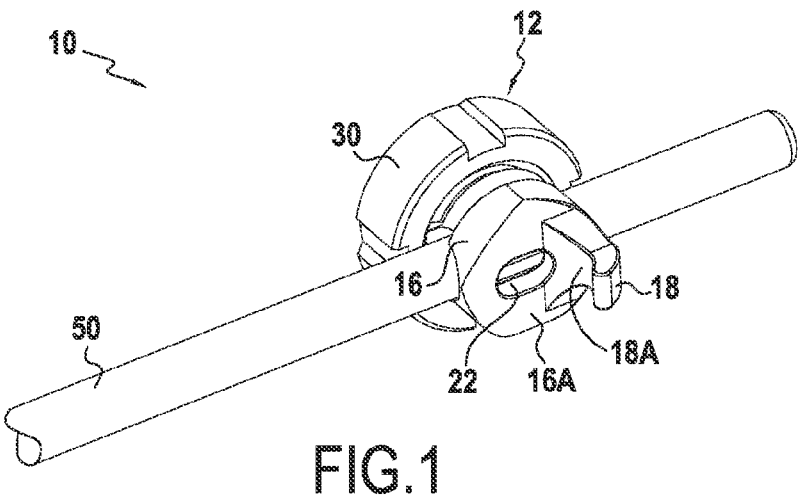
FIG. 1 is a perspective view of an example of stabilization system, in which only one anchor is shown, the flexible member of this anchor not being shown.

In the following detailed description, reference is made to the accompanying drawings showing several examples of anchors and stabilization systems according to the present disclosure. It is intended that these examples be considered as illustrative only, the scope of the invention not being limited to these examples.

Even if in these examples, the anchors and stabilization systems are placed on vertebrae, such anchors and stabilization systems may be placed on other bony structures.

A first example of stabilization system is shown in FIGS. 1 to 4. This stabilization system 10 is for stabilizing at least two vertebrae V1, V2, i.e. for holding together two vertebrae in a particular relative position, as shown in FIGS. 5 and 6.

Stabilization system 10 comprises:
- a first anchor 12 configured to be fastened to a first vertebra V1,
- a second anchor 14 configured to be fastened to a second vertebra V2, and
- a connection member for connecting the first and second anchors 12, 14 together, thereby providing stabilization between the first and second vertebrae V1, V2.

In this example, the connection member is a rod 50 that, for instance, may be rigid and made of biocompatible metallic material.

Figure 4:
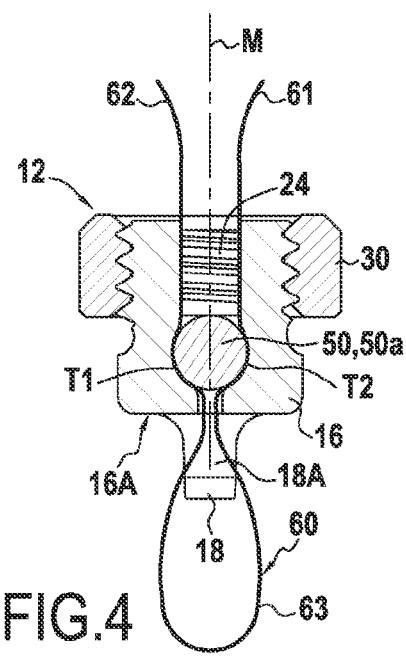
FIG. 4 is a sectional view of the stabilization system of FIG. 1, along plane IV-IV of FIG. 2.
Figure 5:
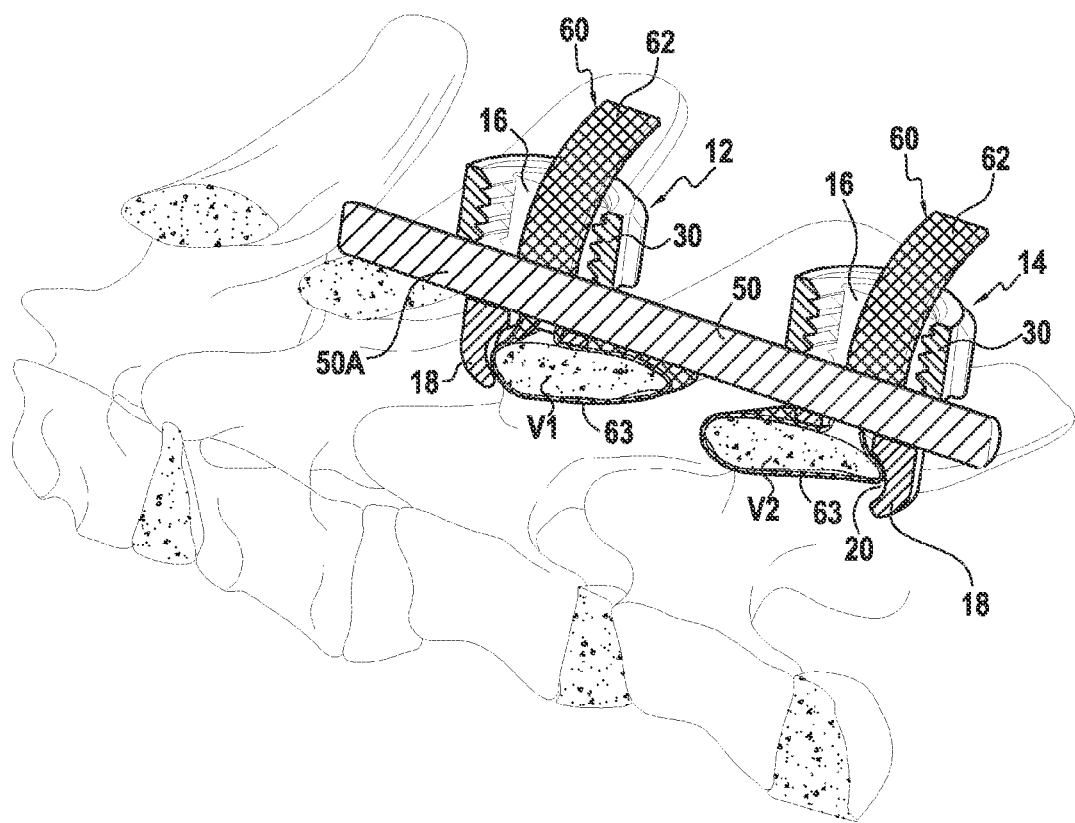
FIG. 5 is a sectional view showing the stabilization system of FIG. 1 in place on two vertebrae, in a compressing configuration.

The second anchor 14 is shown in FIGS. 5 and 6 but not in FIGS. 1 to 4. In this example, the first and second anchors 12, 14 are the same and only the first anchor 12 is described in detail below.

The first anchor 12 comprises: an anchor body 16, a hook 18 that is integral with the anchor body 16 and an elongate flexible member 60. The flexible member 60 is shown only in FIGS. 2, 4, 5 and 6.

Figure 2:
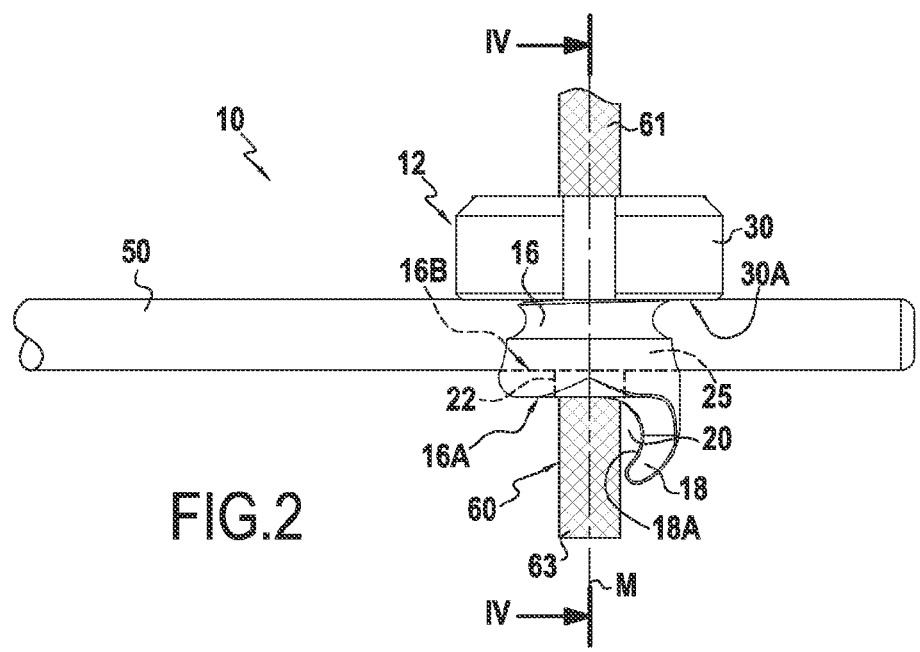
FIG. 2 is a side view of the stabilization system of FIG. 1, the flexible member being shown.
Figure 3:
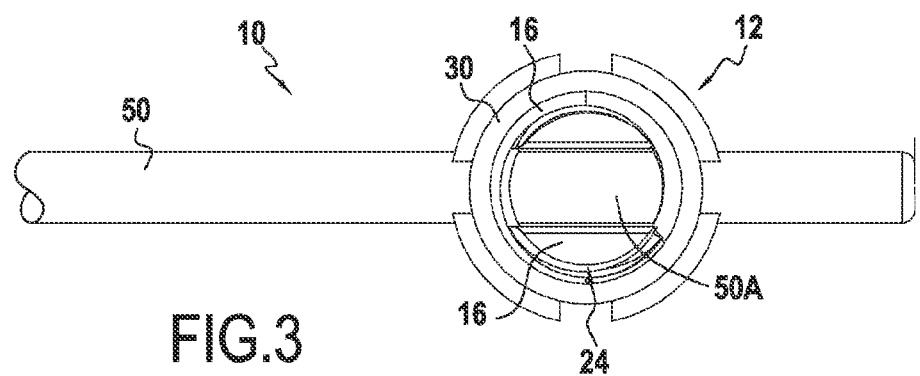
FIG. 3 is a top view of the stabilization system of FIG. 1, the flexible member not being shown.

The hook 18 extends from a first wall 16A, or bottom wall, of the anchor body 16. Lets axis M be the middle axis of the anchor body 16, axis M passing through the center of the first wall 16A as shown in FIG. 2. The hook 18 extends from a peripheral portion of the first wall 16A, away from the axis M, and curves round towards the axis M. Thus, the free end of the hook 18 may become substantially perpendicular to the axis M.

A slot 20 (see FIG. 2) is defined below the anchor body 16, by the internal face 18A of the hook 18 and the first wall 16A. The shape and size of the slot 20 are such that a bony portion of the first vertebra V1 (e.g. a lamina of the vertebra V1) can be inserted into the slot 20.

It is to be noted that the hook 18 may have a different shape. Especially, instead of being curved, the hook 18 may have a straight shape and, for instance, may be a tongue being substantially parallel to the axis M (i.e. with no or small curvature and with no curved end or only a small one). An example of an anchor 12 analogous to that of FIG. 1 but fitted with such a straight hook 18 is shown in FIG. 7. Such a hook still provides a rigid and strong connection to the vertebra (by abutment), with no risk of fatigue phenomena in the connection over time.

With a straight hook 18, the slot 20 is wide open and the hook 18 prevents relative movement between the vertebra and the anchor body 16 along the direction of the rod 50, but not along the direction of the middle axis M. Only the flexible member 60 prevents relative movement between the vertebra and the anchor body 16 along the direction of the axis M (i.e. along the direction perpendicular to the first wall 16A). Since the straight hook 18 is short, when it is positioned onto a lamina of a vertebra, no part of the hook 18 protrudes into the vertebral foramen, which may be advantageous. For instance, such short hooks 18 may be used for the cervical vertebrae.

The flexible member 60 has a first end 61, a second end 62 and an intermediate portion 63 therebetween. The flexible member 60 passes through the anchor body 16 with the first end 61, the second end 62, and the intermediate portion 63 extending outside the anchor body 16.

The anchor body 16 is provided with an exit passage 24 (shown in FIG. 3 and in dotted line in FIG. 4), from which the first and second ends 61, 62 extend. The anchor body 16 is also provided with a loop passage 22 (shown in FIG. 1 and in dotted line in FIG. 2) going through the first wall 16A and opening out in the slot 20, in front of the hook 18. The intermediate portion 63 extends outside, from the loop passage 22. The intermediate portion 63 goes through the slot 20.

In this example, there is only one exit passage 24 and one loop passage 22. However, in other examples (not shown), the anchor body 16 may be provided with two exit passages, one for each end 61, 62 of the flexible member 60. Similarly, the anchor body 16 may be provided with two loop passages, one for each branch of the intermediate portion 63.

The anchor body 16 is further provided with a main passage 25 (shown in FIG. 4 and in dotted line in FIG. 2) for receiving a first portion 50A of the rod 50. The exit passage 24 and the loop passage 22 both communicate with the main passage 25. The exit passage 24 is located above the main passage 25 whereas the loop passage 22 is located below the main passage 25. When the flexible member 60 is passed through the anchor body 16 and the first portion 50A of the rod 50 is placed into the anchor body 16, portions T1, T2 of the flexible member 60 (located between the ends 61, 62 and the intermediate portion 63 of the flexible member 60) are held between the first portion 50A of the rod and the internal wall 16B of the anchor body 16 which defines the main passage 25.

In the example of FIG. 4, the exit passage 24, the main passage 25 and the loop passage 22 are substantially aligned along the middle axis M, and the flexible member 60 passes on each side of the first portion 50A of the rod 50, i.e. a portion T1 of the flexible member 60 passes on the left side of the rod 50 and another portion T2 of the flexible member 60 passes on the right side of the rod 50.

Figure 4A:
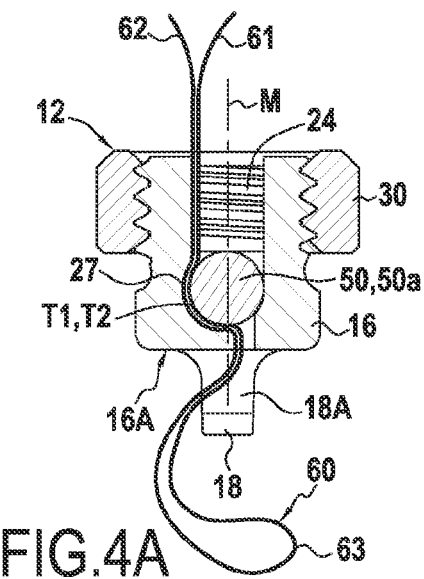
FIG. 4A is a sectional view, analogous to FIG. 4, showing another example of stabilization system.

However, portions T1 and T2 of the flexible member 60 may pass on the same side of the rod 50 as shown in FIG. 4A. In this case, if necessary, the main passage 25 of the anchor body 16 may be provided with a recess 27 in the internal wall 16B, on the corresponding side of the rod 50, so as form an enlarged passage between the internal wall 16B and the rod 50, for passing the two superimposed portions T1, T2, of the flexible member 60. In this case, the loop passage 22 may be shifted with respect to the middle axis M, so as to increase the surface for clamping the flexible member 60, between the anchor body 16 and the rod 50. In the example of FIG. 4A, the loop passage 22 is shifted to the right, so as to increase the clamping surface on the left side of the rod 50.

The first anchor 12 further comprises a locking member 30 for engagement with the anchor body 16. The locking member 30 is a nut provided with an inside thread for rotary engagement with an outside thread provided on the anchor body 16, so that the first portion 50A of the rod 50 may be clamped between the locking member 30 and the anchor body 16 by moving the locking member 30 relative to the anchor body 16. More precisely, in the example, the rod portion 50A is clamped between the internal wall 16B of the anchor body 16, and the lower face 30A of the locking member 30. When the first portion 50A of the rod 50 is clamped inside the main passage 25, the flexible member 60 is simultaneously clamped between the first portion 50A and the anchor body 16.

The locking member 30 is located opposite to the hook 18 with respect to the main passage 25, i.e. the main passage 25 is located between the locking member 30 and the hook 18, which makes the locking member 30 accessible and easy to handle when the hook 18 is placed on a vertebra. Thus, in FIGS. 4 and 4A, the locking member 30 is located above the main passage 25, whereas the hook 18 is located below the main passage 25.

Turning now to FIGS. 5 and 6, the stabilizing system 10 is shown in position on two vertebrae V1, V2.

In FIGS. 5 and 6, the first anchor 12 has been fastened to the first vertebra V1 as follows: the flexible member 60 has been passed around a bony portion of the first vertebra V1 and through the anchor body 16; the first portion 50A of the rod 50 has been positioned into the main passage 25 of the anchor body 16; the rod 50 and the first anchor 12 have both been brought closer to the bony portion of the first vertebra V1 by pulling on the first and second ends 61, 62 of the flexible member 60 (if need be, by means of a tensioning device); the hook 18 has been hooked on said bony portion; further tension has been applied to the flexible member 60 by pulling on its first and second ends 61, 62; and the rod 50 and flexible member 60 have been locked in position relative to the anchor body 16 by tightening the locking member 30.

It is to be noted that the place of the vertebra on which the hook 18 is hooked is surrounded by the flexible member 60. So, a part of the flexible member 60 is wedged between the hook 18 and the vertebra and there is no direct contact between the hook and the vertebra.

The joint action of the hook 18 and flexible member 60 leads to a unique non-invasive anchor, in which the stability provided by the flexible member 60 strengthens and enhances the hook features, and wherein the hook 18 prevents fatigue phenomena over time.

The second anchor 14 may be fastened to the second vertebra V2 in the same way as for the first anchor 12, or in a slightly different way. Especially, when the first anchor 12 is first put in place on vertebra V1, the anchor body 16 of the second anchor 14 is hooked on the bony portion of the second vertebra V2 before loading the second portion 50B of the rod 50 into the anchor body 16.

In FIG. 5, the first and second anchors 12, 14, are placed on adjacent vertebrae V1, V2, and the slot 20 of one anchor 12 (14) faces the other anchor 14 (12). In other words, the slots 20 of the two anchors 12, 14 face each other and the vertebrae V1, V2 are enclosed by the hooks 18. Such a compressing configuration makes it possible to bring the vertebrae V1, V2 closer together, and to hold them together.

In FIG. 6, the first and second anchors 12, 14, are placed on vertebrae V1, V2, which are not adjacent, another vertebra being located between vertebrae V1, V2. The slot 20 of one anchor 12 (14) is opposite to the other anchor 14 (12) with respect to the hook 18. In other words, the slots 20 of the two anchors 12, 14 are oriented in opposite directions and the hooks 18 are enclosed by the vertebrae V1, V2. Such a distracting configuration makes it possible to space the vertebrae V1, V2 and keep them apart.

In the example of FIGS. 5 and 6, vertebrae V1 and V2 are thoracic or lumbar vertebrae. However, the stabilization device of the present disclosure may be used on cervical, thoracic, lumbar or sacral vertebras. The shape and size (length, thickness, curvature, etc.) of the hook 18 and of the slot 20 defined by the hook 18 may be designed depending on the size of the bony portion on which the hook 18 is to be positioned. For instance, hooks for cervical vertebrae may be smaller than those for lumbar vertebrae.

In FIGS. 5 and 6, each hook 18 is positioned on a lamina of a vertebra but other positioning on the vertebra may be considered.

Figure 8:
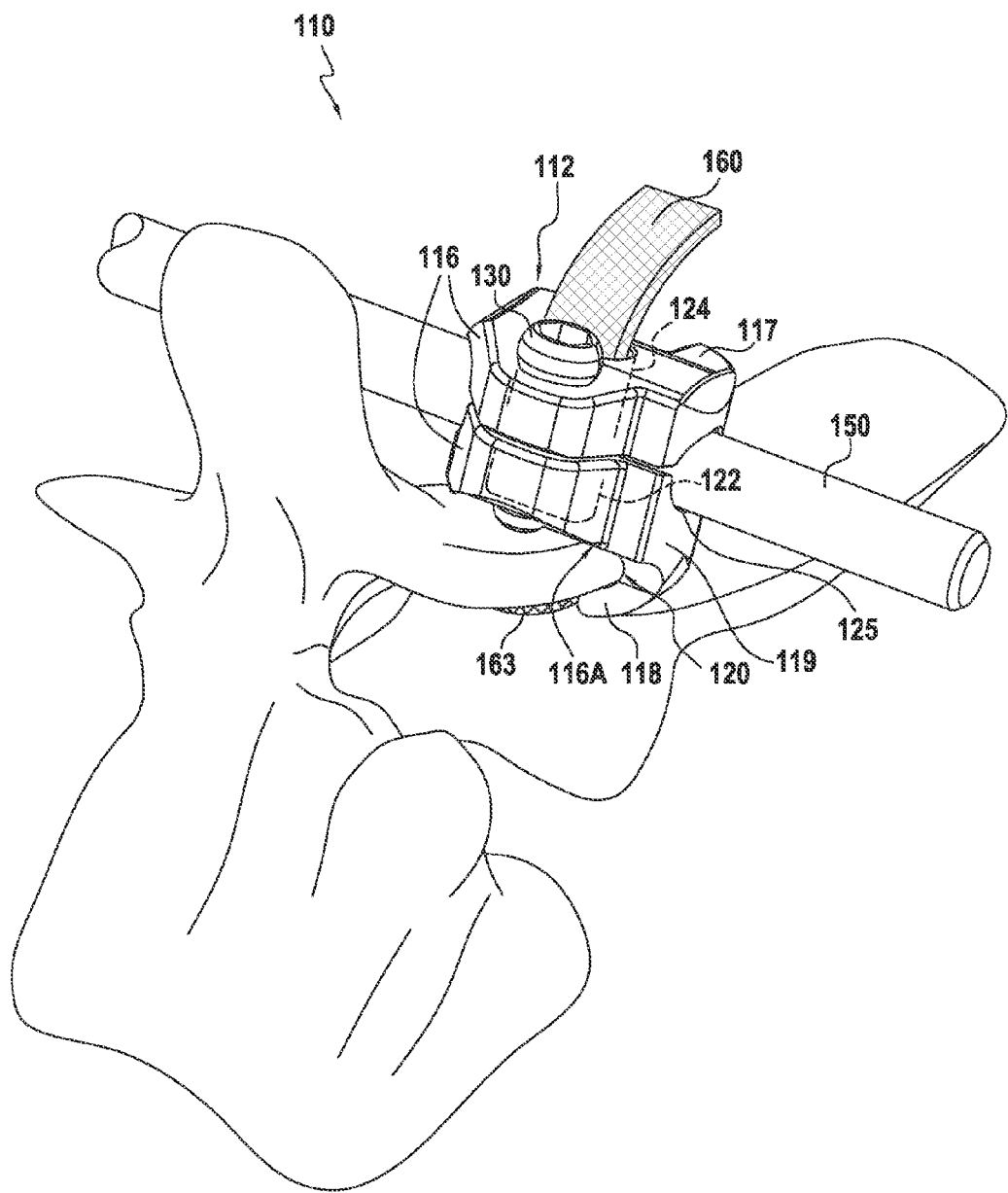
FIG. 8 is a view showing another example of stabilization system in place on one vertebra (only one anchor and one vertebra being shown).
Figure 9:
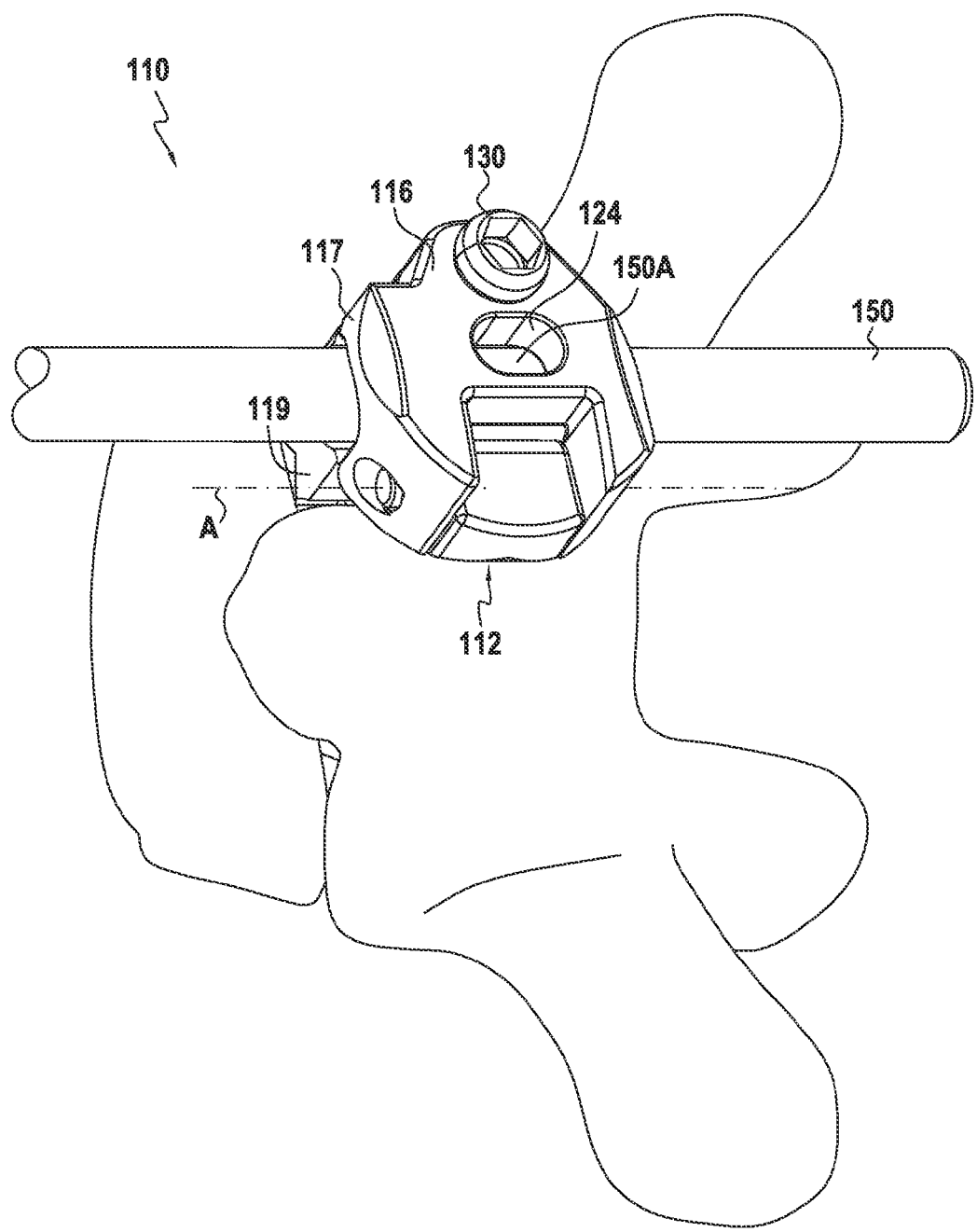
FIG. 9 is another view showing the stabilization system of FIG. 8.

Another example of stabilization system is shown in FIGS. 8 and 9.

This stabilization system 110 comprises:
- a first anchor 112 configured to be fastened to a first vertebra V1,
- a second anchor (not shown) configured to be fastened to a second vertebra (not shown), and
- a connection member for connecting the first and second anchors together, thereby providing stabilization between the first and second vertebrae.

In this example, the connection member is a rod 150 like that of FIG. 1.

The second anchor, which is not shown, may be the same as, or different from, the first anchor 112. When different, the second anchor may be of any type. For instance, the second anchor may be a conventional hook, a system such as that of PCT application no 2009/047352, or a pedicular screw.

The first anchor 112 comprises: an anchor body 116, a hook 118 which is integral with the anchor body 116 and a flexible member 160.

The first anchor 112 differs from the first anchor 12 of FIG. 1 in the following.

The anchor body 116 comprises first and second parts 117, 119 also called upper and lower parts, respectively. These two parts 117, 119 are hinged together around a pivot axis A (shown in chain dotted line in FIG. 9). Thus, the anchor body 116 is movable between a closed configuration, in which the first and second parts 117, 119 are folded (as shown in FIGS. 8 and 9), and an open configuration in which the first and second parts 117, 119 are unfolded. In the closed configuration, the first and second parts 117, 119 define between them a main passage 125 for receiving a first portion 150A of the rod 150.

The hook 118 extends from a first wall 116A, or bottom wall, of the second part 119 of the anchor body 116.

The flexible member 160 is similar to that of FIG. 1. The flexible member 160 is shown in FIG. 8 but not in FIG. 9.

The anchor body 116 is provided with an exit passage 124 going through its first part 117 and from which the first and second ends 161, 162 of the flexible member 160 extend. The anchor body 116 is also provided with one loop passage going through its second part 119 and the first wall 116A, and opening out in the slot 120, in front of the hook 118. The intermediate portion 163 of the flexible member 160 extends outside, from the loop passage.

The exit passage 124 and the loop passage 122 both communicate with the main passage 125. In the closed configuration, the exit passage 124 is located above the main passage 125, whereas the loop passage 122 is located below the main passage 125. After the flexible member 160 is passed through the anchor body 116, the first portion 150A of the rod 50 is placed into the anchor body 116, and the anchor body 116 is moved to the closed configuration. Then, portions of the flexible member 160 are held between the first portion 150A of the rod 150 and the first and second parts 117, 119.

The first anchor 112 further comprises a screw 130 as a locking member. The screw 130 has a shank going through the first and second parts 117, 119, and a head having a profile that allows the screw 130 to be driven in rotation. The screw shank is provided with an outside thread for rotary engagement with an inside thread provided in the second part 119. By tightening the screw 130, the first and second parts 117, 119 are moved from the open to the closed configuration and, thus, the first portion 150A of the rod 150 is clamped inside the main passage 125, between the first and second parts 117, 119, while the flexible member 160 is simultaneously clamped between the first portion 150A and the first and second parts 117, 119.

The screw head bears on top of the first part 117. Therefore, the screw head is located opposite to the hook 118 with respect to the main passage 125, which makes it accessible when the hook 118 is placed on a vertebra.

What is claimed:

1. An anchor for attachment to a bony structure, the anchor comprising:
   an anchor body;
   a hook; and
   a fastening system for fastening a connection member to the anchor body;
   wherein a slot is defined between the hook and a first wall of the anchor body, said first wall facing the hook, the slot being configured to receive a bony structure and the hook being configured to rest on the bony structure;
   wherein the anchor further comprises a flexible member having a first end, a second end and an intermediate portion therebetween, the flexible member passing through the anchor body with the first and/or second end and the intermediate portion extending outside the anchor body;
   wherein the anchor body is provided with at least one exit passage from which the first and/or second end extends, and at least one loop passage going through the first wall and communicating with the slot, the intermediate portion extending from the loop passage to form a loop going through the slot and around said bony structure; and
   wherein the hook is configured to engage the bony structure such that the bony structure is received in the slot while the fastening system is fastening the connection member and the flexible member within the anchor body.

2. The anchor of claim 1, wherein the intermediate portion goes along an internal face of the hook, such that the intermediate portion is fitted between the hook and the bony structure.

3. The anchor of claim 1, wherein the hook is integral with the anchor body.

4. The anchor of claim 1, wherein the anchor body is provided with a main passage configured to receive a portion of the connection member.

5. The anchor of claim 4, wherein the exit passage and the loop passage communicate with the main passage, so that the flexible member passes between the portion of the connection member and the anchor body.

6. An anchor for attachment to a bony structure, the anchor comprising:
   an anchor body;
   a hook; and
   a fastening system for fastening a connection member to the anchor body;
   wherein a slot is defined between the hook and a first wall of the anchor body, said first wall facing the hook, the slot being configured to receive a bony structure and the hook being configured to rest on the bony structure;
   wherein the anchor further comprises a flexible member having a first end, a second end and an intermediate portion therebetween, the flexible member passing through the anchor body with the first and/or second end and the intermediate portion extending outside the anchor body;
   wherein the anchor body is provided with at least one exit passage from which the first and/or second end extends, and at least one loop passage going through the first wall and communicating with the slot, the intermediate portion extending from the loop passage to form a loop going through the slot and around said bony structure;
   wherein the anchor body is provided with a main passage configured to receive a portion of the connection member; and
   wherein the fastening system comprises a locking member for engagement with the anchor body, the locking member engaging with the anchor body so as to clamp the portion of the connection member inside the main passage and to clamp, at the same time, the flexible member between the anchor body and the portion of the connection member.

7. The anchor of claim 6, wherein the locking member is located opposite to the hook with respect to the main passage.

8. The anchor of claim 1, wherein the anchor is a vertebral anchor for attachment to a vertebra.

9. A stabilization system for stabilizing at least two vertebrae, the system comprising:
   the anchor of claim 1, configured to be fastened to a first vertebra;
   a second anchor configured to be fastened to a second vertebra; and
   a connection member for connecting the first and second anchors together, thereby providing stabilization between the first and second vertebrae.

10. The stabilization system of claim 9, wherein the connection member is a rod.

11. A method for stabilizing at least two vertebrae, comprising the steps of:
- providing a stabilization system including:
  - a first anchor comprising:
    - an anchor body;
    - a hook; and
    - a fastening system for fastening a connection member to the anchor body;
    - wherein a slot is defined between the hook and a first wall of the anchor body, said first wall facing the hook, the slot being configured to receive a bony structure of a first vertebrae and the hook being configured to rest on the bony structure;
    - wherein the anchor further comprises a flexible member having a first end, a second end and an intermediate portion therebetween, the flexible member passing through the anchor body with the first and/or second end and the intermediate portion extending outside the anchor body;
    - wherein the anchor body is provided with at least one exit passage from which the first and/or second end extends, and at least one loop passage going through the first wall and communicating with the slot, the intermediate portion extending from the loop passage to form a loop going through the slot and around said bony structure;
  - a second anchor configured to be fastened to a second vertebra; and
  - a connection member for connecting the first and second anchors together, thereby providing stabilization between the first and second vertebrae;
- impeding relative movement between the first anchor and the first vertebra by fastening the first anchor to the first vertebra, by means of said flexible member and hook;
- impeding relative movement between the second anchor and a second vertebra by fastening the second anchor to the second vertebra; and
- impeding relative movement between the first and second anchors by connecting the first and second anchors together, by means of the connection member.

12. The method of claim 11, wherein the step of fastening the first anchor to a first vertebra comprises the sub-steps of passing the flexible member around a bony portion of the first vertebra and through the anchor body, applying tension to the flexible member by pulling on the first and/or second ends of the flexible member and hooking the hook on the bony portion.

13. The method of claim 12, wherein a portion of the flexible member is fitted between the hook and the bony portion.

14. The method of claim 11, wherein the connection member is first connected to the first anchor, the connection member and the first anchor then both being brought closer to the first vertebra by applying tension to the flexible member.

15. The method of claim 11, wherein the anchor body is provided with a main passage configured to receive a portion of the connection member and the fastening system comprises a locking member for engagement with the anchor body.

16. The method of claim 15, further comprising:
- engaging the locking member with the anchor body so as to clamp the portion of the connection member inside the main passage and to clamp, at the same time, the flexible member between the anchor body and the portion of the connection member.

17. The method of claim 11, wherein the stabilization system is used for distracting the first and second vertebrae, the first anchor being placed so that its hook is between its slot and the second anchor.

18. The method of claim 11, wherein the stabilization system is used for compressing the first and second vertebrae, the first anchor being placed so that its slot is oriented toward the second anchor.

* * * * *